United States Patent [19]
Blackburn

[11] Patent Number: 5,190,533
[45] Date of Patent: Mar. 2, 1993

[54] BIODEGRADABLE FLUID-ABSORBING STRUCTURES

[76] Inventor: William A. Blackburn, 102 Biscayne Cir., Cary, N.C. 27513

[21] Appl. No.: 817,159

[22] Filed: Jan. 6, 1992

[51] Int. Cl.$^5$ .................... A61F 13/15; A61F 13/20; B32B 5/16
[52] U.S. Cl. .................... 604/367; 604/358; 604/378; 604/385.1; 428/284; 428/913; 428/402
[58] Field of Search ............... 604/358, 367, 374, 378, 604/375, 385.1, 377, 381; 428/284, 402, 913

[56] References Cited

U.S. PATENT DOCUMENTS

| | | | |
|---|---|---|---|
| 3,777,759 | 12/1973 | Oehmke et al. | 604/372 |
| 4,176,667 | 12/1979 | Herring | 604/375 |
| 4,699,823 | 10/1987 | Kellenberger et al. | 604/378 |
| 4,944,734 | 7/1990 | Wallach | 604/358 |
| 5,009,650 | 4/1991 | Bernardin . | |
| 5,026,363 | 6/1991 | Pratt . | |

Primary Examiner—David Isabella
Assistant Examiner—Paul Zuttarelli
Attorney, Agent, or Firm—Olive & Olive

[57] ABSTRACT

The invention discloses a biodegradable fluid-absorbing structure in which the primary fluid barrier in the structure is a unique utilization of a material in the outer cover of the structure which forms a fluid barrier when exposed to a fluid exuded by an absorbent center section of the structure. The biodegradable fluid-absorbing structure of the invention is suitable for use in a disposable diaper, sanitary napkin, bed pan liner and the like, and is also flushable.

33 Claims, 2 Drawing Sheets

BIODEGRADABLE FLUID-ABSORBING STRUCTURES

BACKGROUND OF THE INVENTION

1. Field of the Invention

This invention relates to fluid-absorbing structures for use in items such as disposable diapers and the like, which are biodegradable and flushable.

2. Description of the Related Art

While the fluid-absorbing structures of the invention are illustrated and described as applicable to use in disposable diapers, it is recognized that the fluid-absorbing structures may be utilized in a number of different products, for example, sanitary napkins, bed liners, bed pan liners, absorbent cloths, and the like.

While there are a number of different disposable diapers on the market, several generalizations about the characteristics of a conventional disposable diaper can be described. A conventional disposable diaper comprises a top sheet which serves as an inner porous liner, a fluid absorbent center ply and a liquid impermeable bottom cover. The top sheet is typically formed from a nonbiodegradable nonwoven fabric produced from a type of synthetic fiber, such as polyester or polypropylene fibers, and typically has a weight of approximately 0.7 oz/yd$^2$. The fluid absorbent center ply of a conventional disposable diaper is predominantly a cellulosic absorbent fluff produced from low density softwood fluff fibers or from blends of softwood and hardwood fluff fibers. Frequently a nonbiodegradable superabsorbent hydrocolloid material is blended into the fluff fibers of the center ply to improve the wicking rate and fluid-holding capacity of the cellulosic fluff in the center ply. Typically the nonbiodegradable superabsorbent material is a polyacrylic acid derivative. The bottom cover of a conventional disposable diaper comprises a monolithic nonbiodegradable film manufactured from polyolefins, such as polyethylene, ranging in thickness of approximately 1 to 1.2 mils.

Prior art patents address virtually all aspects of the disposable diaper. The patent of Bernardin (U.S. Pat. No. 5,009,650), for example, describes an absorbent batt for use in disposable diapers having at least two layers of cellulosic fibers which have different densities or pore sizes, and optionally a superabsorbent material layer. The patent of Pratt (U.S. Pat. No. 5,026,363) describes a disposable diaper having a disassembly or separation means by which the diaper layers are separated and made flushable.

Conventional disposable diapers, however, are not without problems. First, conventional disposable diapers are not biodegradable. While claims of biodegradability are made about some diapers, often the diapers are not fully biodegradable because each and every component is not subject to biodegradation. Second, diapers which utilize biodegradable materials often do not perform adequately in controlling and retaining the fluids introduced into them. For example, diapers having layers comprised of biodegradable films, such as those manufactured from polyvinyl alcohol, are problematic in that the films are water soluble and do not adequately act as fluid barriers to aqueous challenges.

Conventional disposable diapers are typically said to be nonbiodegradable due to the presence of the various non-biodegradable components: the synthetic materials used in the top sheets, the superabsorbents used in the center plys, and the bottom covers comprised of polyolefin films. Many inventors have attempted to provide a biodegradable diaper which both absorbs fluids adequately and is biodegradable. A first problem in creating alternatives to nonbiodegradable disposable diapers, however, is in defining "biodegradable".

Controversy surrounds the definition of "biodegradable". A material is frequently said to be "biodegradable" if when exposed to certain microorganisms, the material is converted into "compost", a process called "composting". The term "biodegradable" has been applied to a converted material even if only a small percentage of the material is actually converted. A material is only fully biodegraded when the microorganisms have depleted all food value from the material. Once all the food value has been depleted from the material, the natural mineral dirt called "humus" remains. Materials which are said to be nonbiodegradable are incapable of being comsumed by microorganisms. As used in this description, the term "biodegradable" is meant to refer to a material which is capable of being entirely consumed by microorganisms to form humus within a relatively short period, for example, six (6) weeks. Additionally, in this description, the terms "biodegradable" and "compostable" are used interchangeably.

The producers of disposable diapers are actively pursuing the development of disposable diapers which are more compatible with the environment by trying to develop biodegradable and flushable diapers. Criticism has been lodged against the use of disposable diapers by environmental protection groups who claim that disposable diapers do not degrade in the landfills and essentially remain unchanged in the ground forever. Several states have threatened to prohibit the sale of disposable diapers; some states have passed legislation to tax disposable diapers in order to cover the cost of disposing of the diapers.

The disposable diaper has, nevertheless, been a boon to the modern parent. The convenience of using disposable diapers as an alternative to reusable (e.g., cloth) diapers has led to an almost total conversion to disposable diapers. In addition to the convenience, disposable diapers have virtually eliminated the discomfort of diaper rash, a skin irritation associated with the use of reusable diapers. A recent article addresses the issue of disposable versus reusable diapers (*Consumer Reports*, August 1991, pp. 551-556).

A second problem in developing an improved disposable diaper is to create a biodegradable disposable diaper which is adequate as a fluid barrier or fluid retainer. In this context, a fluid barrier is a layer of a substance which is impervious to fluid leakage, such as a polyolefin film in a diaper bottom cover. A fluid retainer is a layer of a substance which holds fluid within it, such as a center ply containing a superabsorbent. The polyolefin bottom cover of the currently available disposable diaper is an excellent fluid barrier, but it is not nonbiodegradable. The bottom cover of a disposable diaper must act as a fluid barrier to prevent fluid leakage from the center ply to the outside of the diaper.

One proposed solution to the problem of poor degradability of the disposable diaper has focused on modifying the diaper bottom cover by the addition of a biodegradable component, such as starch, to the polyolefin film which contains high molecular weight segments that do not biodegrade. It is believed that in biodegradation, when the microorganisms attack the biodegradable starch component, the polyolefin film will be broken down into smaller segments which are more compatible with the environment. Because the addition of starch tends to weaken the film, however, a thicker film is utilized in the diaper bottom cover. Therefore, the net amount of diaper bottom cover which is actually biodegraded is slight.

Because portions of conventional disposable diapers are nonbiodegradable, i.e., will not be consumed by microorganisms to form humus, other degradation methods for degrading conventional diapers are sought. However, other degradation methods, such as photodegradation, thermal degradation and hydrolytic degradation, are also inadequate methods because it is becoming more difficult to expose waste products, especially those in landfills, to the proper degradation conditions, such as light, heat and water.

The invention recognizes that the geotextile industry has for many years used sodium bentonite in liners which form fluid barriers in land fills or in ponds to prevent fluid leakage from the landfills or ponds to the surrounding ground areas. Of course, the objective of these geotextile liners, unlike that for a diaper, is to engineer as durable a system as possible and to purposely avoid biodegradation. These geotextile liner products are designed to remain virtually unchanged for more than 30 years as required by recent EPA legislation. The liners are heavy systems weighing approximately one pound per square foot and supposedly can resist hydrostatic pressures equivalent to 150-foot head pressure of water. Examples of such liners are: the CLAYMAX ® liner of the James Clem Corporation of Chicago, Ill.; a liner made by Colloid Environmental Technologies Company of Arlington Heights, Ill.; and a liner made by Gundle Company of Houston, Tex.

The invention recognizes that a conventional disposable diaper could be made more biodegradable in a practical sense if the fluid barrier section could be made of biodegradable substrates which together create an outer cover which prevents fluid leakage, is relatively strong, and provides a pleasant fabric feel. As will become apparent from later description, the invention is based upon the discovery that sodium bentonite, even though never before used, so far as is known, in a disposable diaper or similar fluid-absorbing structure, can be incorporated as a fluid barrier in the outer cover of a disposable diaper when such outer cover is made of biodegradable substrates, thereby making an outer cover which resists fluid leakage, and most importantly, is a biodegradable diaper component. The use of a biodegradable substrate creates a diaper outer cover which has a pleasant fabric texture, rather than the harsh synthetic texture of polyolefin films used in a conventional disposable diaper.

A typical geotextile liner has a layer of sodium bentonite sandwiched between two layers of nonbiodegradable fabric layers, such as heavy-weight polyethylene or polypropylene, which layers are bonded with a degradation-resistant binder or by needlepunching. The liner may be applied to the bottom of a cavity, for example, a landfill or pond. When the geotextile liner becomes wet, the sodium bentonite in the liner becomes gelatinous and swells to approximately twelve times its original volume. The swelled sodium bentonite in the geotextile liner aids in sealing the cavity.

Sodium bentonite has been found to operate as a fluid barrier in the presence of salt contaminants (product literature of Colloid Environmental Technologies Company of Arlington Heights, Ill.), in blends with sand (described by J. Hocks, *Journal of Waste Management Research*, 5(2), pp. 93–105, 1987), and when blended with vermiculite (Chemical Abstracts, CA78:P75483d). Sodium bentonite is also a popular gellant in the oil well drilling industry where it is used to seal walls of oil wells during the drilling process (American Petroleum Institute, Specification 13A).

Sodium bentonite is not known to be harmful to humans or to the environment, as indicated by its use in an antiperspirant formulation, described in U.S. Pat. No. 4,840,786 of Johnson and Baker. Repeated inhalations of sodium bentonite dust in high concentrations may affect the lungs; however, no adverse effects on skin contacts with sodium bentonite have been reported so far as applicant is aware. Sodium bentonite is thus recognized by the invention as being an inorganic mineral which can be introduced into the environment through disposal processes without harming the environment.

Sodium bentonite, an inorganic clay-type mineral, has been assigned Chemical Abstract identification number CAS #1302-78-9. Sodium bentonite is a powder having a pale-buff or grayish tint and a slightly earthy taste. The density of sodium bentonite is approximately 2.5 g/cm$^3$. Sodium bentonite is insoluble in water and in organic solvents. Sodium bentonite swells to approximately twelve times its dry volume when wet with an aqueous fluid. It is a member of the silicate family and is frequently present in volcanic minerals. Sodium bentonite is available under a wide range of trade names including: ALBAGEL, PREMIUM USP 4444, BENTONITE L, ACCOFLOC 352, AQUAGEL, PANTHER CREEK BENTONITE, SOUTHERN BENTONITE, ASKANGEL, VOLCLAY BENTONITE BC, VOLCLAY, WILKINITE, BAROCO, BULGARBEN BA, COSINTAM 403, BENTONITE MAGMA, FULBENT 570, HMP 20, K43, MINERAL COLLOID 101, B-236, and ACCO 2585.

SUMMARY OF THE INVENTION

The invention in the described representative embodiments is directed to a fully biodegradable fluid-absorbing structure for use in a disposable diaper, and the like, which is flushable and whose components are biodegradable. In a broad sense, the fluid-absorbing structure of the invention is comprised of: a biodegradable porous inner liner, a biodegradable absorbent center ply secured to the inner liner, and a biodegradable outer cover, secured to the center ply, comprising a biodegradable back sheet and a material capable of rapidly forming a fluid barrier when contacted by a liquid and operatively associated with the back sheet. As will be seen from the subsequent description, the material may be operatively associated to the back sheet in any number of ways. In the description, "outer cover" is meant to refer to the layers which comprise the fluid barrier section of the invention structure.

The discovery of the invention is the use of an inorganic mineral, sodium bentonite, as an effective fluid barrier in the outer cover of a fluid-absorbing structure such that a fluid-impervious, nonbiodegradable layer (e.g., polyolefin film used in a conventional disposable diaper) is unnecessary in the structure of the invention. The outer cover of the invention structure prevents virtually all fluid leakage from the fluid-absorbing structure, and thus acts as a fluid barrier. The invention also recognizes that the use of sodium bentonite makes effective fluid barriers of biodegradable substrates which if used without sodium bentonite, are ineffective fluid barriers because they typically absorb fluids or are soluble in them, and thus have heretofore been considered inappropriate substrates for use as fluid barriers.

The inorganic mineral sodium bentonite is set forth in this description as the fluid barrier material and described as the material in inorganic mineral layer and the inorganic mineral in the sealant, however, it is recognized that other materials may meet the described characteristics of the invention. Sodium bentonite rapidly forms a fluid barrier when contacted with a liquid, so far as is known is not harmful to human skin, and is relatively inexpensive.

The outer cover of the invention structure comprises biodegradable layers, and inorganic mineral layers. The inorganic mineral layers may be dry layers sifted between the biodegradable layers, or layers which are coated onto the biodegradable layers. Together, the inorganic mineral layers and the biodegradable layers create an outer cover which prevents virtually all fluid leakage from the structure and thus eliminates the need for a biodegradable fluid-impervious bottom cover.

In addition to the structure of the invention being biodegradable, it is also flushable. Through the use of a conventional household garbage disposal unit, it has been discovered that the unique and biodegradable fluid-absorbing structure of the invention may be shredded into fragments that will flush down the drain and process satisfactorily through sanitary sewage or septic tank systems. A slightly modified blade in a conventional household garbage disposal entirely shreds the invention structure into small particles and eliminates the yarns of material which are produced by shredding with an unmodified disposal.

The fluid-absorbing structure of the invention may also be shredded in hydropulpers presently used in paper recycling. Hydropulpers are used as a first step in the recycling process of certain paper products in which the products to be recycled are shredded and liquified. In a conventional hydropulper, a high-speed flat, circular, toothed blade is rotated in a tank of water. The objects to be pulped are added through the top of the tank and released through a screen located at the bottom of the tank. The size of the screen apertures controls the size of the particles which are released. Such hydropulpers may be utilized as a first step in the disposal process of biodegradable fluid-absorbing structures of the present invention by shredding and liquifying the structures, after which time they may be introduced into sanitary sewage systems. The invention structures are suited to being shredded in this manner. Similarly, a homogenizer, presently used for paper shredding or paint preparation, may be utilized to shred the structures. A homogenizer uses a flat blade with teeth to grind material in a liquid. For use with the invention structure, the homogenizer may be manually held in the toilet bowl or may be attached to a lever arm which lowers the homogenizer into the bowl to shred the structure into flushable fragments.

It is therefore an object of the invention to provide a fluid-absorbing structure which is entirely biodegradable.

It is also an object of the invention to provide a biodegradable fluid-absorbing structure which is also flushable.

Further objects and advantages will become apparent as the following description proceeds with reference to the accompanying drawings and examples.

DETAILED DESCRIPTION OF THE INVENTION AND THE PREFERRED EMBODIMENTS THEREOF

Figure 1:
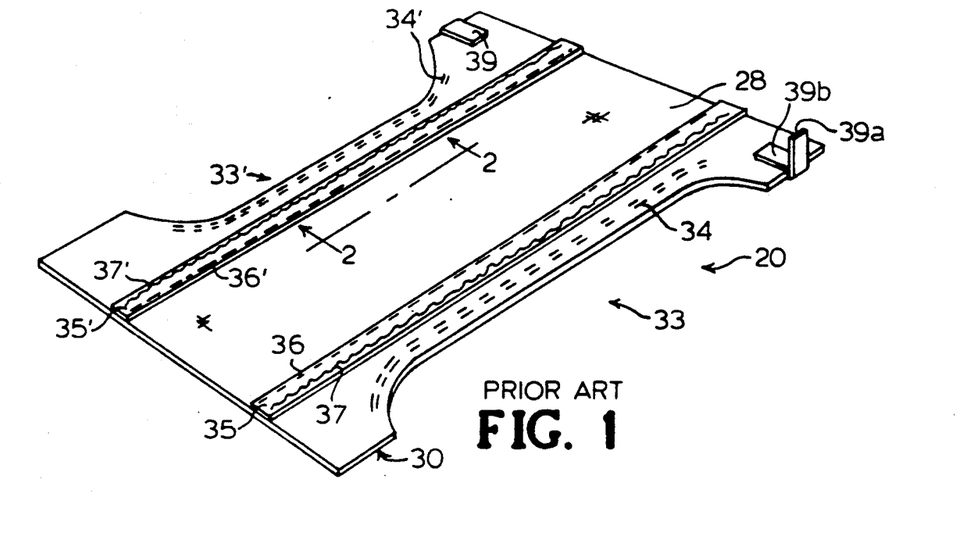
FIG. 1 is a perspective view of a presently available disposable diaper.
Figure 2:
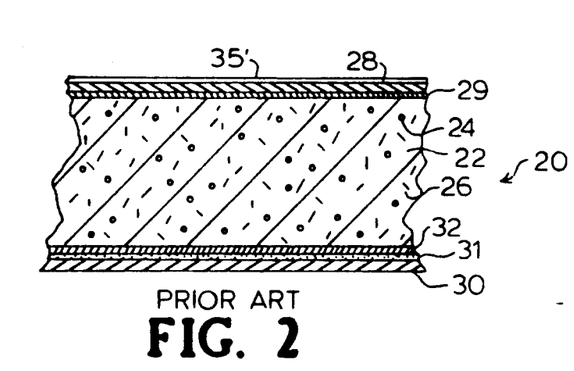
FIG. 2 is a section view taken along lines 2—2 of the prior art diaper shown in FIG. 1.

A currently available disposable diaper 20, is shown for illustrative purposes only in FIGS. 1 and 2, and used for comparison of absorbency and structure with the fluid-absorbing structure of the invention. Diaper 20 is a Procter and Gamble disposable diaper product, marketed as ULTRA-PAMPERS TM (12 to 24-pound boy's diaper). Diaper 20 is reportedly produced using the technology described in U.S. Pat. Nos. 3,848,549; B1 3,860,003; 4,081,301; 4,573,986; 4,578,071; 4,610,678; B1 4,662,875; 4,834,735; and RE 32,649.

As shown in section view in FIG. 2, diaper 20 is comprised of top sheet 28, center ply 22 and bottom cover 30. Top sheet 28 is a thermally-bonded polypropylene nonwoven fabric weighing approximately 0.7 oz/yd$^2$. Center ply 22 comprises a powder superabsorbent material 24 added into an absorbent cellulosic fluff 26. Bottom cover 30 is a 1.2 mil polyethylene film having a light blue cover with a matte finish. Top sheet 28 and center ply 22 are lightly thermally bonded to tissue paper 29. Bottom cover 30 and center ply 22 are lightly adhesively bonded to a lightweight tissue paper 32 through the use of an adhesive bead 31 on approximately 0.5-inch centers running the length of the diaper 20, which bonds through tissue 32 to center ply 22. Leg cut outs 33 and 33', FIG. 1, are gathered elastic portions 34 and 34', respectively, to aid in the fit of diaper 20 around the wearer's legs. Leg cuffs 35 and 35' attach to top sheet 28 at seams 37 and 37', respectively, and are gathered with elastic 36 and 36', respectively, to further improve the fit of diaper 20 and resist fluid leakage. Tab 39 has pressure-sensitive adhesive surface 39a which adheres to releasable surface 39b. Tab 39 is pulled from releasable surface 39b and adhered to the front of diaper 20 (not shown) to enclose diaper 20 around the wearer.

As previously stated, the biodegradable fluid-absorbing structure of the invention may be incorporated into a number of different absorbent structures; however, by way of example, the detailed description which follows describes the use of the biodegradable fluid-absorbing structure in a disposable diaper.

Figure 3:
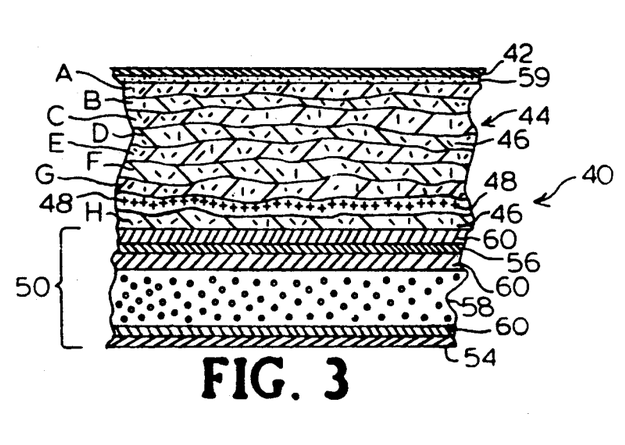
FIG. 3 is a section view of a first embodiment of the invention illustrating the layers comprising the fluid-absorbing structure of the invention.

A cross-section of a first embodiment of the biodegradable fluid-absorbing structure 40 of the invention in the form of a disposable diaper is shown in FIG. 3. Inner liner 42, touches the wearer's body, and is therefore designed to be a comfortable layer. Fluid introduced into inner liner 42 passes through inner liner 42 and is trapped in center ply 44.

Porous inner liner 42 is preferably constructed of nonwoven fabric made from a natural fiber, for example, from staple-length cotton or rayon. The invention recognizes that these natural fibers lend themselves to being bonded in a variety of methods to form the nonwoven fabric, for example, a mechanical bonding method such as hydroentangling, or a method of bonding the fibers with a water soluble biodegradable binder. The invention recognizes that water soluble binders tend to release the bound fibers when sheared in water, thus making this type of nonwoven fabric suitable for shredding for future flushing, and thus particularly suitable for use as the inner liner 42.

Biodegradable nonwoven fabrics suitable for use as inner liner 42 include hydroentangled 100% cotton fabric weighing approximately 1.1 oz/yd$^2$, hydroentangled 100% cotton fabric lightly needlepunched having a weight of approximately 1.5 oz/yd$^2$, 100% cotton 0.6 oz/yd$^2$ carded nonwoven fabric which is saturation bonded, and hydroentangled nonwoven fabric formed from a blend of approximately 40% cellulose and 60% cotton.

The invention also recognizes that a cotton or rayon nonwoven fabric which is made from fibers having a hydrophobic finish, such as a fluorocarbon finish is uniquely suited to serving as inner liner 42. Heretofore, such hydrophobic-finished fibers were believed to be nonbiodegradable. Fabrics made from fibers having hydrophobic finishes are desirable in applications such as disposable diapers because the finishes give the fabrics their stay-dry properties, i.e., fluid passes through the fabric and does not come back through the fabric thus making the fabric dry to the touch. Recently, the results of a study which investigated the composting properties of such a group of nonwoven fabrics were revealed (Wilkes, A. G. and Meekin, L. J. of Courtaulds Research, United Kingdom at the INDA Waste Management Conference, Washington, D.C., Sep. 24-25, 1991, Conference Book of Papers). The study tested the composting properties of both hydroentangled 100% medical-grade cotton, hydroentangled rayon prepared with and without hydrophilic and hydrophobic finished fibers, 20% by weight latex-bonded rayon and cotton nonwoven fabrics, and thermally-bonded blends of rayon and polypropylene. The composting properties of these fabrics were compared to the similar weighted polyester and polypropylene nonwoven fabrics. The cotton and rayon fabrics were found to be compostable and the synthetic fabrics resisted degradation. The hydrophobic-finished rayon fibers were degraded at a slightly slower rate than the hydrophilic-finished rayon fibers, but the degrees of degradation were similar. The latex-bonded fabrics showed delayed degradation, but were eventually composted. These differences in degradation rates were smaller in anaerobic (in the absence of free oxygen) digesters than in compost heap exposures. In light of this study, the invention recognizes that another suitable biodegradable fabric for use as inner liner 42 is also found in a 0.6 oz/yd$^2$ cotton nonwoven fabric which is a carded lightweight latex-bonded nonwoven fabric, obtained from Sterns Technical Textiles of Cincinnati, Ohio.

Adhesive 59 is used on inner liner 42 to secure inner liner 42 to center ply 44 and to strengthen inner liner 42. Adhesive 59 bonds the absorbent cotton nonwoven material used as inner liner 42 and ultimately creates a stronger fabric with a pleasant fabric feel. Adhesive 59 is preferably a biodegradable adhesive prepared from a stock solution of polyvinyl alcohol (PVOH) and a commercially available adhesive (see Example 1). A suitable PVOH is a product of Air Products and Chemicals, Inc. of Allentown, Pa. A suitable adhesive is AIRVOL ™ 205. When certain of the above-described nonwoven cotton fabrics are utilized as inner liner 42, for example, lightly needlepunched 100% cotton, adhesive 59, FIG. 3, is of particular advantage because without adhesive 59, the fabric fibers tend to separate if rubbed. Adhesive 59 is preferably sprayed onto the fabric prior to assembly in the fluid-absorbing structure 40.

Center ply 44, according to a first embodiment of fluid-absorbing structure 40, FIG. 3, is secured to inner liner 42 and comprises an absorbent substrate 46 and a biodegradable organic fluid-absorbent material 48. Absorbent substrate 46 is preferably formed from an absorbent material, for example, cellulosic fluff or absorbent cotton. Cellulosic fluff is preferred as substrate 46 because it absorbs satisfactorily and is more economical in cost. In the first embodiment, substrate 46 is shown as multiple layers A through H.

A suitable biodegradable organic fluid-absorbent material 48 is a derivative of carboxy-methyl-cellulose (CMC). CMC is available in granular, fiber and powder form, any of which forms may be used as organic fluid-absorbent material 48. Organic fluid-absorbent material 48 is preferably sifted between the bottom layers G and H of absorbent substrate 46, FIG. 3, or layers F and G (not shown). This placement of organic fluid-absorbent material 48 between the bottom layers of substrate 46 allows maximum opportunity for absorbent substrate 46 to absorb the fluid and slow the fluid flow rate, thus maximizing the absorbency properties of organic material 48. If the fluid passes too quickly through substrate 46, organic material 48 does not have an opportunity to absorb all the passing fluid.

It is with regard to the fluid barrier section of the structure 40, outer cover 50, where the heart of the invention lies. The heart of the invention is the recognition that an inorganic mineral, particularly sodium bentonite, provides an effective fluid barrier in the outer cover 50 of the biodegradable fluid-absorbing structure 40. With the use of the inorganic mineral, the fluid-barrier properties of outer cover 50 are so effective that the need for a nonbiodegradable fluid-impervious bottom cover, of the kind utilized in a conventional disposable diaper, is eliminated. Elimination of the bottom cover of a conventional disposable diaper is seen as a tremendous advantage because the fluid-impervious bottom cover is non-biodegradable. Furthermore, the bottom cover of a conventional disposable diaper has a synthetic feel, and does not provide a breathable cover. As will be seen from the description to follow, the disposable diaper construction of the invention substantially avoids these kinds of considerations.

Outer cover 50 of the invention structure resists fluid leakage because sodium bentonite in the outer cover 50 swells upon wetting to form a fluid barrier. When the sodium bentonite swells, it seals the area which it covers so that no fluid passes through, and thus forms a fluid barrier.

Sodium bentonite is set forth as an example, and discussed as the preferable inorganic mineral; however, other materials having similar properties, particularly the hydration properties of sodium bentonite, would be suitable as the fluid barrier material used in outer cover 50. Calcium bentonite, however, is not a suitable inorganic mineral for use in outer cover 50 because its hydration properties prevent it from being an adequate fluid barrier. Calcium bentonite hydrates more slowly and less effectively than sodium bentonite, and thus does not act as an effective fluid barrier in outer cover 50.

Because of its low cost, a sodium bentonite coated layer is an attractive alternative to the polypropylene film bottom cover used in the current disposable diaper. Based on current prices, the sodium bentonite component appropriate for one disposable diaper would cost less than approximately 0.5 cents per diaper. The current cost per diaper for polyethylene backing is approximately 4.0 cents per diaper. A suitable sodium bentonite formulation for use in the outer cover 50 of the invention is AQUAGEL TM, from Baroid Company of Houston, Tex., although as previously indicated, many formulations of sodium bentonite are available and are equally suitable.

According to the first embodiment of the invention, FIG. 3, the sodium bentonite is utilized as a dry layer to form inorganic mineral layer 58 and as a component of sealant 60. Outer cover 50 is comprised of several operatively associated layers: back sheet 54 which is coated on one side with sealant 60; inorganic mineral layer 58 which is applied, for example, by sifting, to back sheet 54; and intermediate substrate 56 which is coated on both sides with sealant 60 and applied to inorganic mineral layer 58.

When fluid is introduced into structure 40 at inner liner 42, it passes into center ply 44. In center ply 44, fluid is absorbed and retained by absorbent substrate 46 and organic fluid absorbent material 48, thus capturing the fluid in center ply 44. Any fluid which leaks out of center ply 44 to intermediate substrate 56 is obstructed by the inorganic mineral in the sealant 60 which coats substrate 56. The mineral once mixed in sealant 60 is in a swollen state and thus seals the pores of intermediate substrate 56, and prevents or retards any fluid from passing through the substrate 56. Any fluid which passes through the coated intermediate substrate 56 then enters the inorganic mineral layer 58. Because fluid is temporarily held in intermediate substrate 56, inorganic mineral layer 58 can absorb any fluid passing into it at an optimal rate. If the fluid is introduced into inorganic mineral layer 58 without being slowed by the inorganic mineral component of sealant 60, the inorganic mineral in layer 58 does not have an opportunity to swell to its optimum capacity. The inorganic mineral in layer 58 swells, and further seals the outer cover 50 to prevent fluid leakage. Finally, any fluid passing through layer 58 is prevented from further leakage by the inorganic mineral component of sealant 60 upon back sheet 54.

In addition to acting as a fluid barrier, sealant 60 also aids in binding intermediate substrate 56 to center ply 44 and inorganic mineral layer 58, and back sheet 54 to inorganic mineral layer 58. While a more simple adhesive than sealant 60 is also suitable, for example, adhesive 59 previously identified, or a spray starch solution, preferably sealant 60 comprising the inorganic mineral is used so that the fluid-barrier properties of sealant 60 can be employed.

Sealant 60 comprises PVOH, sodium bentonite, glycerin and water. Industry practice in applications unrelated to the present invention suggests that if more than 7% by weight sodium bentonite is used in a composition of sodium bentonite in water, the composition does not create a suitable paste. The addition of glycerin and PVOH to the paste comprised of sodium bentonite and water allows an unexpectedly large amount of sodium bentonite to be added without sacrificing the performance of the paste. It is recognized that acceptable sealant compositions can be achieved from a wide range of concentrations of the ingredients. Such ranges in percentages by weight include mixtures of the following: 7% to 20% by weight of sodium bentonite, 5% to 20% by weight of polyvinyl alcohol, 1% to 10% by weight of glycerin and 87% to 50% by weight of water; and the formulation 10% to 17% by weight of sodium bentonite, 8% to 17% by weight of polyvinyl alcohol, 3% to 8% by weight of glycerin and 79% to 58% by weight of water. Although it is recognized that various concentrations would achieve similar results, a suitable paste formulation for sealant 60 is as follows: in percentage by weight, sodium bentonite 16.0%, polyvinyl alcohol 16.5%, glycerin 5.3% and water 62.2%. Any percentage references in formulations found in the description are meant to indicate percentage by weight.

The invention recognizes that many variations in layer placement, and a variety of substrate materials are suitable to achieve an effective fluid barrier in outer cover 50. Only a sampling of the various combinations are described in the description, it being appreciated that many variations of the preferred embodiments described herein are possible without departing from the spirit of the invention.

For example, the invention recognizes that suitable materials for back sheet 54 and intermediate substrate 56 are the natural nonwoven fabrics described above in relation to inner liner 42, for example, hydroentangled cotton or rayon, lightly needlepunched cotton bonded with adhesive 59, cotton carded nonwoven, hydroentangled cellulose/cotton or rayon blends or laminates, or hydrophobic-finished nonwoven cotton or rayons. Other suitable materials for back sheet 54 and intermediate substrate 56 are paper, such as newspaper print or paper towel structures based on cellulose sources, or biodegradable films such as PVOH films. These materials are preferred because they are biodegradable and they provide a pleasant fabric feel. It is particularly important, as a practical matter, that back sheet 54 have a pleasant fabric feel.

Figure 4:
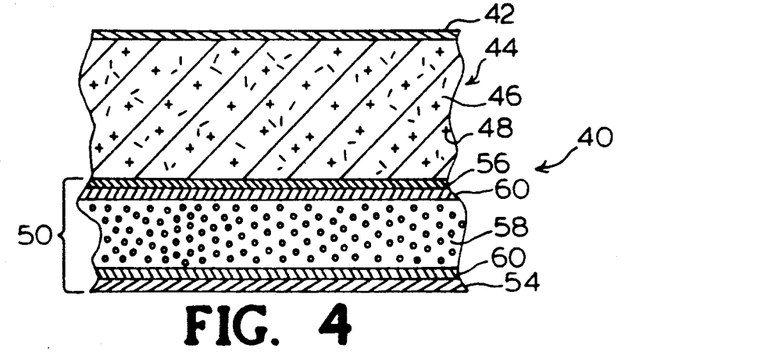
FIG. 4 is a section view of a second embodiment of the invention.

According to a second embodiment, FIG. 4, adhesive 59 is not applied to inner liner 42, it being understood that adhesive 59 is not an essential component to creating a suitable inner liner 42. The suitable materials used for inner liner 42, intermediate substrate 56, and back sheet 54 in the first embodiment are equally suitable for use in the second embodiment. The invention, according to the second embodiment, recognizes that suitable center ply 44 comprises an absorbent substrate 46 which is a single batt structure into which organic fluid-absorbent material 48 is blended, rather than a layered substrate 46 as described in the first embodiment. This embodiment for center ply 44 is preferred because the absorbency of organic material 48 is maximized and because currently available manufacturing procedures make this embodiment feasible.

The second embodiment of structure 40 of the invention also recognizes that sealant 60 need coat only one side of intermediate substrate 56. It is preferable that intermediate substrate 56 be coated on at least one side so that a lesser amount of dry inorganic mineral layer 58 is used in outer cover 50 to keep the overall weight of structure 40 down. Sealant 60 is shown, FIG. 4, applied to intermediate substrate 56 between intermediate substrate 56 and inorganic mineral layer 58 to help bind substrate 56 to layer 58, and causes the layers to be operatively associated. Additionally, as previously discussed, sealant 60 on intermediate substrate 56 forms a fluid barrier between center ply 44 and layer 58, and retards the fluid flow rate through outer cover 50.

Figure 5:
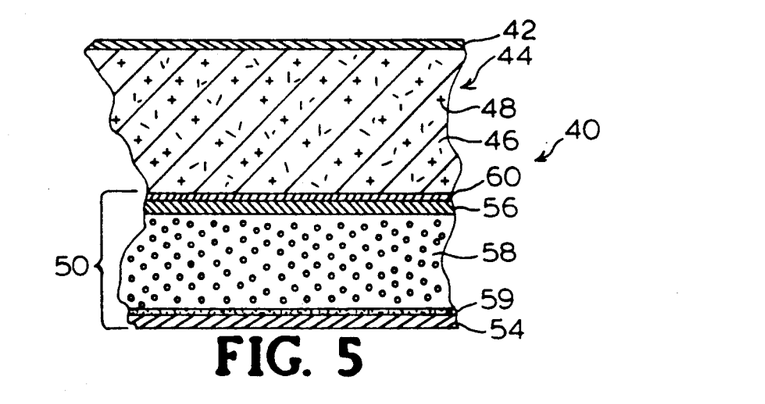
FIG. 5 is a section view of a third embodiment of the invention.

According to a third embodiment, FIG. 5, structure 40 differs from the second embodiment in that sealant 60 is applied to intermediate substrate 56 between intermediate substrate 56 and center ply 44. Sealant 60 aids in binding substrate 56 to center ply 44 and more importantly, prevents fluid leakage and retards the flow rate of any fluid which may pass through center ply 44. According to the third embodiment, adhesive 59 is applied to back sheet 54 to bind back sheet 54 to inorganic mineral 58. Adhesive 59 strengthens back sheet 54, as previously described in relation to the inner liner 42 treated with adhesive 59, and gives back sheet 54 a pleasant fabric feel.

Figure 6:
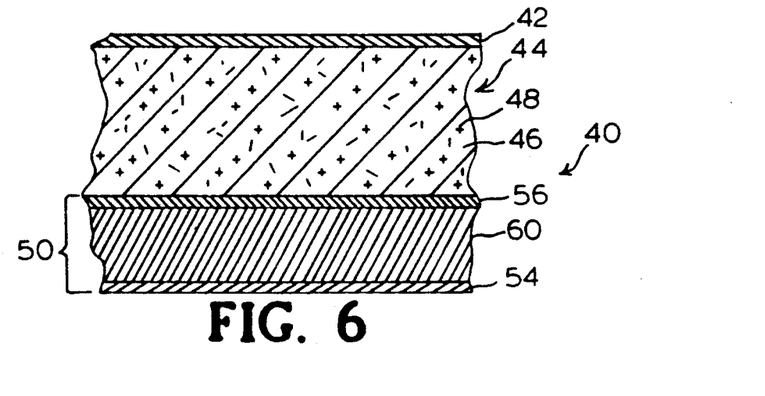
FIG. 6 is a section view of a fourth embodiment of the invention.

In a fourth embodiment, FIG. 6, outer cover 50 contains no dry inorganic mineral layer 58. In some cases, a layer 58 of dry inorganic mineral may not be desired because of possible shifting of the layer in transporting structure 40 once manufactured and packaged. Additionally, it is sometimes difficult from a manufacturing standpoint to sift solid materials, although there are numerous examples where this process is successful.

To accommodate the absence of the fluid barrier provided by inorganic mineral layer 58, sealant 60 must be applied in an adequate amount and in a uniform manner in outer cover 50. In the fourth embodiment, sealant 60 is applied to back sheet 54 onto which intermediate substrate 56 is placed, thus completing outer cover 50. In this embodiment, the biodegradable films and paper substrates work particularly well as back sheet 54 and as intermediate substrate 56, because of the ease with which sealant 60 is applied to these materials. The materials allow sealant 60 to be applied in a uniform manner in an adequate amount.

EXAMPLE I

The biodegradable fluid-absorbing structure 40 of the invention utilizes two substances as an adhesive: a polyvinyl alcohol (PVOH) adhesive 59 and sealant 60 (comprised of sodium bentonite, glycerin, polyvinyl alcohol and water). Sealant 60, having sodium bentonite, also functions as a fluid barrier as well as an adhesive.

A PVOH adhesive is prepared by adding solid adhesive AIRVOL TM 205 to tepid water and heating the mixture with agitation in a boiling water bath until the solution is complete. The PVOH solution is subsequently diluted to a 5% concentration by the addition of water, thereby converting the adhesive to a sprayable formulation, indicated in the description as adhesive 59.

Sealant 60 may be comprised of only sodium bentonite and water. This mixture can contain a maximum concentration of approximately 7% by weight sodium bentonite in water since any higher concentration causes the mixture to gel from a liquid to a solid and will not provide the most ideal paste for use in the structure 40 of the invention.

To strengthen the sealant 60 coating and to lower the viscosity of the paste, PVOH is added to the water-sodium bentonite mixture, thus creating a sealant comprising PVOH, sodium bentonite and water. A suitable paste adhesive is formed containing, in percentage by weight, 6% PVOH, 7% sodium bentonite, and 87% water. Upon drying, however, the dried film is somewhat stiff and may crack as the sodium bentonite hydrates. To avoid this cracking effect, glycerin is added to the mixture.

When glycerin is added to the sealant paste it (1) plasticizes the PVOH and improves the paste's flexibility, and (2) serves as a humectant to maintain the sodium bentonite in a partially hydrated gelled state where its fluid barrier properties are best performed. Glycerin may be replaced by a less expensive glycol (e.g., ethylene glycol, polyethylene glycol or polypropylene glycol) but glycerin is preferred because of its low toxicity. Glycerin is widely used in the food industry as an edible component. However, the glycerin could be replaced with the various glycols so long as properties of biodegradability, proper viscosity and film formation are maintained. For example, as the molecular weight of the glycol component increases, the sealant becomes nonbiodegradable, loses its viscosity and its good film-forming properties.

Various amounts of glycerin are suitable in the PVOH/sodium bentonite mixture. Glycerin is added in percentages by weight as follows: at 0%, 1.5%, 3.5% and 7.0%. Each sealant solution is stirred to form a smooth uniform gray-colored paste. To test the stiffness of each paste, the sealant is applied to 8.5×11.0-inch lined sheets of common notebook paper. (Each sheet before being coated weighs approximately 3.35 g). The sealant is brushed onto both sides of the paper. The coated weights after air drying overnight are approximately 4.04 g, 3.90 g, 4.08 g and 4.06 g for the 0%, 1.5%, 3.5% and 7.0% glycerin concentrations respectively. To test the flexibility of the material, the coated papers are cut into 1-inch strips. The bending length is determined by sliding the strips of paper over a sharp end and allowing the paper to bend until the weight of the unsupported strip causes the paper to bend to an angle of 45°. A very flexible material bends rapidly when only a small distance of the strip is pushed over the edge. A stiffer material requires that more of the specimen be pushed over the edge before the same end point is reached. The larger the bending length number, the stiffer the specimen. Results are shown below in Table 1.

TABLE 1

| Glycerin (%) by weight | 0 | 1.5 | 3.5 | 7.0 |
|---|---|---|---|---|
| Bending Length (inches) | 5.4 | 5.1 | 5.1 | 3.8 |

Based on these results, it is recognized that concentrations of greater than 3.5% of glycerin are required to reduce the stiffness of the system. Additionally, these results are surprising in light of technical literature which suggests that additions of glycerin as low as 2% will plasticize the PVOH and reduce the stiffness of the system. To achieve optimal flexibility for outer cover 50 of the invention, a concentration of 7% glycerin is utilized.

When a mixture of 15 g sodium bentonite, 30 g of 25% PVOH, 10 g of glycerin, and 100 g of water is mixed, the viscosity is significantly reduced when compared to the system with water alone. The amount of sodium bentonite can be doubled to 30 g without exceeding viscosity limits needed for effectively applying the mixture onto various substrates. At this higher sodium bentonite concentration, coatings are weaker such that upon drying, the surfaces crack and give a discontinuous, and therefore, unsatisfactory paste. However, increasing the amount of 25% PVOH to 50 g cures this problem. The resulting paste doctors smoothly onto substrates and resists cracking upon drying.

A standardized recipe for the higher concentration of sodium bentonite and PVOH is as follows, in percentage by weight: sodium bentonite 16.0%; polyvinyl alcohol 16.5%; glycerin 5.3%; and water 62.2%.

EXAMPLE II

To test the fluid retention properties of the outer cover of the invention, the polyethylene bottom cover of a model diaper is removed and replaced with the invention outer cover, to be tested. First a sample of a porous 100% cotton hydroentangled nonwoven fabric is taped to the back of the diaper to get a base measurement of fluid retention when only a nonwoven fabric is utilized as outer cover 50. The modified diaper is challenged with 100 ml of water containing one drop of blue food coloring (Durkee-French Foods, Inc. of Wayne, N.J.). The blue-colored water breaks through the porous fabric almost immediately. The fluid breakthrough is detected visually and by touching the back of the diaper.

EXAMPLE III

The experiment of Example II is repeated using an alternative outer cover of the invention. A layer of hydroentangled 100% cotton 1.1 oz/yd$^2$ nonwoven fabric is prepared by coating it with the sealant to form a back sheet. The weight of the sealant coating applied is approximately 3 oz/yd$^2$. The dry sodium bentonite is then sifted onto the sealant-coated back sheet so that it evenly spreads over a target area of approximately 9×9 inches in the center of the back sheet. An intermediate substrate is prepared of hydroentangled 100% cotton 1.1 oz/yd$^2$ nonwoven fabric and coated on one side with the sealant. The coated side of the intermediate substrate is placed onto the sifted sodium bentonite. The sample is laminated by placing it between two layers of approximately 1 mil polyethylene film, covering the sample with a glass plate, and pressing with a weight of approximately 10 pounds for about 30 minutes. The weight, glass, and film are removed, and the sandwich is allowed to air dry overnight. The sandwich obtained is flexible and easy to handle.

The challenge with 100 ml of colored water described in Example II is repeated. When challenged, the outer cover prevents fluid leakage. Neither a visual nor a touch inspection reveals any fluid leakage through the outer cover after approximately two hours.

EXAMPLE IV

In the previous example, a considerable amount of the sealant is used in closing the pores in the intermediate substrate of 100% cotton hydroentangled nonwoven fabric. In a more economical combination, a less porous material of newsprint paper is used as the intermediate substrate.

A 7.5×8.5-inch rectangle of newsprint paper weighing 2.5 g, is coated on both sides with 7.7 g of the sealant to form the intermediate substrate. The coated paper is placed on a reduced amount of dry sodium bentonite, 10 g instead of 40 g, which has been sifted over a 9×9-inch target area of a sealant-coated back sheet of 100% hydroentangled cotton. To accelerate drying, this sample is laminated using an electric iron at a low temperature setting. When the system is challenged with water as in the previous Example III, it prevents fluid leakage.

EXAMPLE V

EXAMPLE IV is repeated using as the back sheet 100% absorbent cotton 1.5 oz/yd$^2$ nonwoven fabric which is lightly "tack bonded" by needling, and is additionally bonded using the binder spray adhesive (adhesive 59). Prior to bonding with the 5% PVOH, the fabric is very weak and has very poor abrasion resistance. After PVOH spraying and drying, the strength and abrasion resistance are dramatically improved. The weight of PVOH added is 0.24 oz/yd$^2$. The back sheet is then sealant-coated and prepared with 10 g of sifted sodium bentonite. The back sheet of this Example prevents fluid leakage and has a pleasant fabric feel.

EXAMPLE VI

In this example, as the intermediate substrate, a 9×10-inch sample of drawing paper, weighing approximately 10.23 g per sheet, (National Paper Company, Style No. 42-010) is precoated with the sealant. The coated drawing paper is applied to a back sheet. The back sheet is the sealant-coated PVOH bonded 100% absorbent cotton nonwoven described in Example V. This system is tested as before and is resistant to fluid leakage.

EXAMPLE VII

In this example, a polyvinyl alcohol (PVOH) film is used as the intermediate substrate. The back sheet is a 100% cotton nonwoven which has been sprayed with the 5% PVOH spray adhesive (adhesive 59) and coated with the sealant. Ten grams of dry sodium bentonite are sifted onto the back sheet. PVOH film is coated on one side with the sodium bentonite sealant, which side is subsequently placed onto the dry sodium bentonite. When tested as before, this outer cover system prevents fluid leakage.

EXAMPLE VIII

In this example, the outer cover of the invention is formed by applying the sealant to a 5% PVOH sprayed 100% cotton hydroentangled nonwoven fabric as the intermediate substrate. Ten grams of the dry sodium bentonite is applied to the back sheet of 5% PVOH sprayed 100% cotton hydroentangled nonwoven fabric and covered with the coated intermediate substrate. This system when tested as before is found to prevent fluid leakage.

It is obvious from the results obtained in Examples I-VIII that a large number of combinations of outer cover substrates including sealant layers, could be expected to perform satisfactorily. The back sheet and intermediate substrates could be different as well as the same materials. A number of paper, film, and fabric combinations give satisfactory results. Also, in place of the PVOH binder used in these examples, alternative binders could be selected from the growing number of biodegradable binders being made available. A suitable adhesive alternative is the naturally occurring starch binders which tend to be the most economical binders available.

EXAMPLE IX

In this example, the dry sodium bentonite layer in the outer cover of the invention is eliminated and replaced with a paste sodium bentonite layer. Paste or liquid-coating systems are normally preferred over dry coating layers primarily because the liquid coatings can be controlled to make uniform layers. Liquid coatings are generally more economical as a result because thinner more uniform coatings are obtainable and thus cost less. In the case of the sodium bentonite systems, the coating must be thoroughly mixed to reduce lumps in the clay which lodge under the coating blade and produce streaks in the coating.

The sealant layer is applied to an intermediate substrate by pulling a Gardner knife which is adjusted for a proper coating thickness evenly over the substrate. Layers ranging in thickness from approximately 25 mils to 100 mils provide layer thicknesses adequate for fluid barrier layers; although the effective thickness depends in large part on the substrate material chosen. A thickness of less than 25 mils may be produced if superior mixing machines are used to create the paste. Lower grade mixing machines, however, leave lumps in the mixture which subsequently foul the Gardner knife.

Once a back sheet is laminated to the sealant-coated substrate the system is dried. The viscosity of the sealant is such that penetration of the back sheet by the sealant is avoided. When a wet coating of approximately 100 mils thickness is oven dried to constant weight at 200° F., the dry weight of the coating is approximately 20 oz/yd$^2$. A coating of 75 mils averages approximately 15 oz/yd$^2$ in weight, 50 mils approximately 10 oz/yd$^2$, and 25 mils approximately 5 oz/yd$^2$.

Particularly suitable intermediate substrate materials are: (1) paper towels such as Procter and Gamble's BOUNTY TM paper towels (made under one or more of U.S. Pat. Nos. 3,905,863; 3,974,025; 4,191,609; 4,446,597; 4,529,486; 4,637,859 and Des. 239,137); (2) ALBANENE TM No. 105351 tracing paper such as of Kevffel and Esser Company, weighing 2.77 g per 8.5×11-inch sheet; (3) drawing paper multiuse Style No. 42-010 of the National Paper Company, weighing 7.6 g per 9×12-inch sheet; and (4) newsprint paper, such as used by the Raleigh News and Observer of Raleigh, N.C., weighing 3.3 g per 8.5×11-inch sheet.

Each paper has its own range of suitable coating thicknesses. For example, newsprint paper is very weak while in the wet state and difficult to handle when coated with 100 mils of coating weighing approximately 20 oz/yd$^2$. With the same thickness of coating, the ALBANENE TM paper tends to wrinkle on wetting and drying, while the drawing paper is stiff and difficult to form into a curved shape. The BOUNTY TM paper towel, however, performs well.

The thinner the coating thickness, the more manageable the substrate. The minimum coating thickness for each paper material is that which permits the substrate to act as a fluid barrier and not permit fluid break through. Determining coating thicknesses may easily be accomplished by one skilled in the art.

EXAMPLE X

In this example, suitable biodegradable films are utilized as the intermediate substrates in the invention structure. Current technical literature contains a growing list of biodegradable film-forming materials (from abstracts from a September, 1991 computer literature search by NERAC, Inc., of Tolland, Conn.). Additionally, suitable substrates are formed from commercially available biodegradable extrudable films such as: a film extruded from Tone P-787 (a polycaprolacton polymer, supplied by Union Carbide Corporation), and an extruded film from Vinex 2034 (a polyvinyl alcohol polymer, supplied by Air Products Corporation). The biodegradability of these extrudable films is discussed in the trade literature (Ryle, T. R., "Extruding Degradable Materials", Conference Book of Papers, INDA Waste Management Conference, Washington, D.C., Sep. 24-25, 1991). Table 3 below lists such films.

TABLE 3

| | |
|---|---|
| 1. | Block copolymers of poly (ethylene succinate) and polytetramethylene glycol |
| 2. | Block copolymers of amylose |
| 3. | Block and graft copolymers of cellulose |
| 4. | Cellophane |
| 5. | Cellulose acetate |
| 6. | Cellulose/starch/polystyrene graft polymers |
| 7. | Chitosan |
| 8. | Collagen |
| 9. | Copolydioxanes |
| 10. | Corn starch |
| 11. | Mater-Bi resin (a starch-based polymer) |
| 12. | Poly (acetaldehyde) |
| 13. | Poly (amide esters) |
| 14. | Poly (anhydrides) (amideanhydrides) |
| 15. | Poly (caprolactone) |
| 16. | Poly (dilactide-diglycolide) |
| 17. | Poly (dilactic-polyacetic acid) |
| 18. | Polyesters of citric acid and glycerin |
| 19. | Polyethylene oxide/polylactic acids |
| 20. | Poly (ethylene succinate)-B-poly (ethylene glycol) |
| 21. | Poly (ethylene succinate)-B-poly (tetramethylene glycol) |
| 22. | Poly-B-hydroxyalkanotes |
| 23. | Poly (hydroxybutyrate) |
| 24. | Poly (3-hydroxybutyrate-3-hydroxyvalerate) |
| 25. | Poly (iminocarbonates) |
| 26. | Poly (isopropyl methacrylate) |
| 27. | Poly (L-lactic acid) |
| 28. | Poly (L-lactic acid/aromatic hydroxy acids) |
| 29. | Poly (D, L-lacic-co-glycolic acid) block copolymers |
| 30. | Poly (methyl methacrylate-co-isopropyl methacrylate) |
| 31. | Poly (orthoesters) |
| 32. | Poly (pyridinium derivatives of poly methyl methacrylate) |
| 33. | Starch acetate |
| 33a. | Poly (sodium vinyloxyacetate) |
| 34. | Poly ((tertiary butyloxycarbonylmethyl) glutamates) |
| 35. | Poly (tetramethylene adipate) |
| 36. | Poly (trimethylene carbonate) |
| 37. | Poly (1-trimethylsilyl)-1-propyne |
| 38. | Poly (vinylpyrolidone) |
| 39. | Viscose rayon |

The extruded film is coated with the sealant in approximately 25 mils thickness. A 5% PVOH-bonded 100% cotton nonwoven fabric is applied to the wet coating as a back sheet. The system is then dried. After drying, the system is liquid challenged. This system prevents fluid leakage adequately.

EXAMPLE XI

In the next example, carboxy-methyl-cellulose (CMC) is utilized as the biodegradable organic fluid absorbent material 48 in center ply 44 of the invention structure. CMC is available in granular, fiber and powder form. Suitable CMC products are those of the Aqualon Corporation, such as: AQUALON TM CMC (granular), AQUASORB TM Absorbent Fiber, and AQUASORB TM A250 powder.

In this example, the CMC grains are used. The AQUALON TM CMC is a sodium salt of carboxymethyl cellulose which has been purified to a 99.5% minimum analysis. It is a white granular material with a very low order of toxicity. The CMC grains are sprinkled at a weight of 5 g of CMC per 40 g of absorbent nonwoven material 46 in center ply 44. The absorbent nonwoven material 46 is cut from 100% cotton nonwoven 1.5 oz/yd$^2$ lightly needlepunched fabric. Cellulosic fluff performs equally as well as the described material 46. Approximately eight layers of this nonwoven fabric are used to provide the 40 g target weight. The CMC grains are sifted onto the second bottom layer of fabric with an effort being made to concentrate the grains in the center of the layer. The remaining layers are then placed over the CMC layer.

A top sheet of 100% cotton 0.6 oz/yd$^2$ saturation-bonded carded nonwoven is placed onto the CMC-prepared center ply. This assembly is next placed over an outer cover for absorbency testing. The outer cover comprises a back sheet of a 5% PVOH spray coated layer of the 1.5 oz./yd$^2$ absorbent cotton nonwoven fabric which is sprayed with 5% of PVOH adhesive to bind 40 g of dry sodium bentonite and also comprises an intermediate substrate of 5% PVOH-bonded absorbent cotton nonwoven. This system is challenged with the blue colored 100 ml aqueous challenge used in previous examples. The CMC performs effectively in controlling the fluid in the system and reduces the tendency of the fluid to be squeezed from the center ply. The outer cover effectively prevents fluid leakage.

EXAMPLE XII

Example XI is repreated using CMC fibers, such as AQUASORB TM Absorbent Fibers, as the CMC component in the center ply of the invention structure. These fibers are made from cotton linters which are carboxymethylated and have fiber lengths of approximately 3 mm. These fibers absorb more than 7 ml of liquid per gram of fibers. Chemical Abstracts has assigned the number CAS 9004-32-4 to this class of products. The CMC fibers are sifted by brushing the fibers through a large-pore screen having openings of approximately ¼ inch. The fibers are collected on the bottom layer of absorbent cotton fabric onto which the remaining seven plys are placed. When challenged with the aqueous challenge, the CMC fibers gel the fluid and retain it in the center ply.

EXAMPLE XIII

This example utilizes a CMC powder, such as AQUASORB TM A250, as the organic fluid absorbent material 48 in the center ply. This free-flowing powder is easy to process and sifts easily into the absorbent cotton plys. This form of CMC rapidly locks up fluids at a lock-up rate of 30–60 seconds. (This is the time required to absorb 20 ml of 1% sodium chloride (NaCl) solution.) The powder has an absorption capacity of 40–75 ml of 1% NaCl per gram of powder. An attractive feature of this absorbent is the absence of chemical cross-linking agents. This material when combined with the cotton absorbent nonwoven material at a rate of 5 g of CMC per 40 g of absorbent nonwoven material results in a center ply which has attractive fluid-holding properties.

Cellulosic fluff as the absorbent nonwoven material yields the same results. All of these center ply combinations perform satisfactorily in composting systems.

A significant advantage of the invention is that the inner liner, the center absorbent section and the outer cover can all be formed of staple length fibers as contrasted to the continuous filament components of the prior art structures. This distinction makes the structure of the invention shreddable and therefore disposable in a conventional sewer system.

While the invention has been described with specific reference to illustrative embodiments and specific features, it will be recognized that the utility of the present invention is not thus limited, but rather extends to other modifications, variations, and embodiments which will be readily apparent to those skilled in the art.

What is claimed is:

1. A biodegradable fluid-absorbing structure, comprising:
   (a) a biodegradable porous inner liner;
   (b) a biodegradable absorbent material forming a central section secured to the inner liner; and
   (c) a biodegradable outer cover secured to the absorbent material comprising:
      (i) a biodegradable back sheet;
      (ii) a biodegradable intermediate substrate located between the back sheet and the absorbent material; and
      (iii) at least one inorganic mineral layer applied between the back sheet and the intermediate substrate and formed of a material which is capable of rapidly forming a fluid barrier when contacted by a fluid exuded by the absorbent material.

2. The biodegradable fluid-absorbing structure according to claim 1 wherein the inorganic mineral layer comprises sodium bentonite.

3. The biodegradable fluid-absorbing structure according to claim 1 wherein the inorganic mineral layer is a sealant comprising 7% to 20% by weight of sodium bentonite, 5% to 20% by weight of polyvinyl alcohol, 1% to 10% by weight of glycerin, and 87% to 50% by weight of water.

4. The biodegradable fluid-absorbing structure according to claim 1 wherein the inorganic mineral layer is a sealant comprising 10% to 17% by weight of sodium bentonite, 8% to 17% by weight of polyvinyl alcohol, 3% to 8% by weight of glycerin, and 79% to 58% by weight of water.

5. The biodegradable fluid-absorbing structure according to claim 1 wherein the inorganic mineral layer is a sealant comprising 16.0% by weight of sodium bentonite, 16.5% by weight of polyvinyl alcohol, 5.3% by weight of glycerin and 62.2% by weight of water.

6. The biodegradable fluid-absorbing structure according to claim 1 of a size adapted for use as a disposable diaper for infants.

7. A biodegradable fluid-absorbing structure, comprising:
   (a) a biodegradable porous inner liner;
   (b) a biodegradable absorbent material forming a center section secured to the inner liner; and
   (c) a biodegradable outer cover secured to the absorbent material comprising:
      (i) a biodegradable back sheet; and
      (ii) a biodegradable intermediate substrate positioned and retained between the back sheet and the absorbent material and coated on at least one side with a biodegradable inorganic mineral sealant, said sealant formed of a material capable of rapidly forming a fluid barrier when contacted by a fluid exuded by the absorbent material.

8. The biodegradable fluid-absorbing structure according to claim 7 wherein the inorganic mineral sealing comprises sodium bentonite.

9. The biodegradable fluid-absorbing structure according to claim 8 of a size adapted for use as a disposable diaper for infants.

10. The biodegradable fluid-absorbing structure according to claim 7 further comprising a biodegradable inorganic mineral layer applied between the intermediate substrate and the back sheet and operatively associated therewith, and being formed from a material which is capable of rapidly forming a fluid barrier when contacted by a fluid exuded by the absorbent material.

11. The biodegradable fluid-absorbing structure according to claim 10 wherein the inorganic mineral layer comprises dry sodium bentonite.

12. The biodegradable fluid-absorbing structure according to claim 11 of a size adapted for use as a disposable diaper for infants.

13. The biodegradable fluid-absorbing structure according to claim 7 wherein the back sheet is also coated with the inorganic mineral sealant.

14. The biodegradable fluid-absorbing structure according to claim 7 wherein the back sheet is coated with a biodegradable adhesive.

15. The biodegradable fluid-absorbing structure according to claim 14 wherein the biodegradable adhesive is a 5% by weight polyvinyl alcohol spray.

16. The biodegradable fluid-absorbing structure according to claim 7 wherein the inorganic material layer is a sealant comprising 7% to 20% by weight of sodium bentonite, 5% to 20% by weight of polyvinyl alcohol, 1% to 10% by weight of glycerin, and 87% to 50% by weight of water.

17. The biodegradable fluid-absorbing structure according to claim 7 wherein the inorganic material layer is a sealant comprising 10% to 17% by weight of sodium bentonite, 8% to 17% by weight of polyvinyl alcohol, 3% to 8% by weight of glycerin, and 79% to 58% by weight of water.

18. The biodegradable fluid-absorbing structure according to claim 7 wherein the biodegradable inorganic mineral sealant comprises 16.0% by weight of sodium bentonite, 16.5% by weight of polyvinyl alcohol, 5.3% by weight of glycerin and 62.2% by weight of water.

19. The biodegradable fluid-absorbing structure according to claim 7 wherein the absorbent material further comprises a biodegradable organic fluid absorbent material.

20. The biodegradable fluid-absorbing structure according to claim 7 wherein the biodegradable back sheet is formed of a material selected from the group consisting of nonwoven cotton, nonwoven rayon, hydroentangled cotton, hydroentangled rayon, bonded absorbent nonwoven cotton, hydrophobic-treated nonwoven cotton, hydrophobic-treated nonwoven rayon, hydroentangled cellulose-cotton blend, hydroentangled cellulose-rayon blend, and paper.

21. The biodegradable fluid-absorbing structure according to claim 7 wherein the biodegradable intermediate substrate is formed of a material selected from the group consisting of nonwoven cotton, nonwoven rayon, hydroentangled cotton, hydroentangled rayon, bonded absorbent nonwoven cotton, hydrophobic-treated nonwoven cotton, hydrophobic-treated nonwoven rayon, hydroentangled cellulose-cotton blend, hydroentangled cellulose-rayon blend and paper.

22. The biodegradable fluid-absorbing structure according to claim 7 wherein the biodegradable intermediate substrate is formed of a material selected from the group consisting of polyvinyl alcohol film, starch polymer film and polycaprolactone.

23. The biodegradable fluid-absorbing structure according to claim 7 wherein the biodegradable inner liner is formed of a material selected from the group consisting of nonwoven cotton, nonwoven rayon, hydroentangled cotton, hydroentangled rayon, bonded absorbent nonwoven cotton, hydrophobic-treated nonwoven cotton, hydrophobic-treated nonwoven rayon, hydroentangled cellulose-cotton blend and hydroentangled cellulose-rayon blend.

24. A biodegradable fluid-absorbing structure, comprising:
(a) a biodegradable porous inner liner;
(b) a biodegradable center section secured to the inner liner and comprising a biodegradable absorbent substrate containing a biodegradable organic fluid absorbent material; and
(c) a biodegradable outer cover secured to the center section comprising:
(i) a biodegradable back sheet coated on one side with a biodegradable inorganic mineral sealant;
(ii) a biodegradable inorganic mineral layer applied to the sealant; and
(iii) a biodegradable intermediate substrate coated on at least one side with the inorganic mineral sealant and secured to the inorganic mineral layer, thereby forming a composite capable of rapidly forming a fluid barrier when contacted by a fluid exuded by the center section.

25. The biodegradable fluid-absorbing structure according to claim 24 wherein the inorganic mineral layer comprises sodium bentonite.

26. The biodegradable fluid-absorbing structure according to claim 24 wherein the inorganic mineral sealant comprises sodium bentonite.

27. The biodegradable fluid-absorbing structure according to claim 24 of a size adapted for use as a disposable diaper for infants.

28. A biodegradable fluid barrier for an absorbent structure, comprising:
a biodegradable back sheet;
(b) a biodegradable inorganic mineral layer applied to the back sheet, wherein the inorganic mineral layer comprises an inorganic mineral capable of absorbing fluids; and
(c) a biodegradable substrate applied to the inorganic mineral layer, thereby forming a composite capable of rapidly forming a fluid barrier when contacted by a fluid.

29. The biodegradable fluid barrier according to claim 28 wherein the inorganic mineral layer comprises sodium bentonite.

30. The biodegradable fluid barrier according to claim 28 further comprising an inorganic mineral sealant comprising sodium bentonite applied to at least one side of the back sheet.

31. The biodegradable fluid barrier according to claim 28 further comprising an inorganic mineral sealant comprising sodium bentonite applied to at least one side of the intermediate substrate.

32. A biodegradable fluid-absorbing structure, comprising:
(a) a biodegradable porous inner liner;
(b) a biodegradable center section secured to the inner liner and formed of a biodegradable absorbent material adapted to receive and absorb fluid passed through the inner liner; and
(c) a biodegradable outer cover secured to the center section comprising:
(i) a biodegradable back sheet; and
(ii) a material operatively associated with the back sheet and located over an area of the back sheet normally exposed to fluid passing from the center section, wherein the material comprises an inorganic mineral capable of absorbing liquids, and thereby being capable of rapidly forming a fluid barrier when contacted by a fluid exuded by the center section.

33. A biodegradable fluid barrier for an absorbent structure, comprising:
   (a) a biodegradable back sheet;
   (b) a biodegradable inorganic mineral layer applied to the back sheet;
   (c) a biodegradable substrate applied to the inorganic mineral layer, thereby forming a composite capable of rapidly forming a fluid barrier when contacted by a fluid; and
   (d) an organic mineral sealant comprising sodium bentonite applied to at least one side of the back sheet or the substrate.

* * * * *

UNITED STATES PATENT AND TRADEMARK OFFICE
CERTIFICATE OF CORRECTION

PATENT NO. : 5,190,533
DATED : March 2, 1993
INVENTOR(S) : William A. Blackburn

It is certified that error appears in the above-indentified patent and that said Letters Patent is hereby corrected as shown below:

Column 19, line 20, delete "material" and substitute --mineral--.

Column 19, line 26, delete "material" and substitute --mineral--.

Column 20, line 34, insert (a) before "a" at beginning of line.

Signed and Sealed this

Twenty-eighth Day of December, 1993

Attest:

BRUCE LEHMAN

Attesting Officer

Commissioner of Patents and Trademarks